United States Patent
Isobe et al.

(10) Patent No.: US 11,124,811 B2
(45) Date of Patent: Sep. 21, 2021

(54) METHOD FOR PRODUCING α-HYDROMUCONIC ACID

(71) Applicant: TORAY INDUSTRIES, INC., Tokyo (JP)

(72) Inventors: Kyohei Isobe, Kamakura (JP); Kenji Kawamura, Kamakura (JP); Masateru Ito, Kamakura (JP); Katsushige Yamada, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 15/580,585

(22) PCT Filed: Jun. 9, 2016

(86) PCT No.: PCT/JP2016/067231
§ 371 (c)(1),
(2) Date: Dec. 7, 2017

(87) PCT Pub. No.: WO2016/199858
PCT Pub. Date: Dec. 15, 2016

(65) Prior Publication Data
US 2018/0223318 A1    Aug. 9, 2018

(30) Foreign Application Priority Data

Jun. 10, 2015    (JP) .............................. JP2015-117345

(51) Int. Cl.
C12P 7/44 (2006.01)
C12N 1/20 (2006.01)

(52) U.S. Cl.
CPC .................. *C12P 7/44* (2013.01); *C12N 1/20* (2013.01); *C12N 1/205* (2021.05)

(58) Field of Classification Search
CPC .............. C12P 7/44; C12N 1/205; C12N 1/20
See application file for complete search history.

(56) References Cited

U.S. PATENT DOCUMENTS

| 2011/0091944 A1* | 4/2011 | Wu ........................ C12P 17/10 435/121 |
| 2013/0095540 A1 | 4/2013 | Burgard et al. |

FOREIGN PATENT DOCUMENTS

| EP | 3214072 A1 | 9/2017 |
| EP | 2265709 B1 | 11/2017 |
| JP | 2011-512868 | * 4/2011 |
| JP | 2011-512868 A | 4/2011 |
| JP | 2011-515111 A | 5/2011 |
| WO | WO 2009/113853 A2 | 9/2009 |
| WO | WO 2013/130487 A2 | 9/2013 |
| WO | WO 2014/043182 A2 | 3/2014 |
| WO | WO 2014/055649 A1 | 4/2014 |
| WO | WO 2016/068108 A1 | 5/2016 |

OTHER PUBLICATIONS

Henry J. Rogers. Iron-binding catechols and virulence in *Escherichia coli*. Infection and Immunity (1973), 7(3): 445-456.*

Harwood et al., "The β-Ketoadipate Pathway and the Biology of Self-Identity," Annu. Rev. Microbiol., vol. 50., 1996, pp. 553-590.

Hyland, "Development of a Platform Strain for Production of Adipic Acid Yields Insights into the Localized Redox Metabolism of *S. cerevisiae*," Thesis—Master of Applied Science, Graduate Dept. of Chemical Engineering and Applied Chemistry, University of Toronto, 2013, pp. 1-47 (53 pages total).

International Search Report and Written Opinion of the International Search Authority (Forms PCT/ISA/210 and PCT/ISA/237) for International Application No. PCT/JP2016/067231, dated Sep. 6, 2016, including an English translation of the International Search Report.

Tanaka et al., "*Desulfovirga adipica* gen. nov., sp. nov., an adipate-degrading, Gram-negative, sulfate-reducing bacterium," International Journal of Systematic and Evolutionary Microbiology, vol. 50, 2000, pp. 639-644.

Extended European Search Report for European Application No. 16807564.6, dated Nov. 23, 2018.

Parthasarathy et al., "Substrate specificity of 2-hydroxyglutaryl-CoA dehydratase from Clostridium symbiosum: toward a bio-based production of adipic acid," Biochemistry, vol. 50, 2011, pp. 3540-3550.

* cited by examiner

*Primary Examiner* — Iqbal H Chowdhury
(74) *Attorney, Agent, or Firm* — Birch, Stewart, Kolasch & Birch, LLP

(57) ABSTRACT

A method of producing α-hydromuconic acid using a metabolic pathway of a microorganism is disclosed. The method of producing α-hydromuconic acid includes the step of culturing at least one type of microorganism having a capacity to produce α-hydromuconic acid, selected from the group consisting of microorganisms belonging to the genus *Escherichia*, microorganisms belonging to the genus *Pseudomonas*, microorganisms belonging to the genus *Hafnia*, microorganisms belonging to the genus *Bacillus*, microorganisms belonging to the genus *Cupriavidus*, microorganisms belonging to the genus *Acinetobacter*, microorganisms belonging to the genus *Alcaligenes*, microorganisms belonging to the genus *Delftia*, and microorganisms belonging to the genus *Shimwellia*.

12 Claims, No Drawings

US 11,124,811 B2

METHOD FOR PRODUCING α-HYDROMUCONIC ACID

TECHNICAL FIELD

The present invention relates to a method of producing α-hydromuconic acid using a microorganism.

BACKGROUND ART

α-Hydromuconic acid (IUPAC name: (E)-hex-2-enedioic acid) is a dicarboxylic acid having a carbon number of 6 and a molecular weight of 144.13. α-Hydromuconic acid can be used as a raw material for polyesters by polymerization with a polyol, or for polyamides by polymerization with a polyamine. By lactamizing α-hydromuconic acid by addition of ammonia to its terminus, it can also be used as a raw material for polyamides by itself.

As a report related to a method of producing α-hydromuconic acid using a microorganism, there is a report disclosing that, during a method of producing adipic acid using succinyl-CoA and acetyl-CoA as starting materials and a non-naturally occurring microorganism, 3-hydroxyadipic acid (3-hydroxyadipate) as an intermediate in an adipic acid biosynthetic pathway is dehydrated by enzymatic reaction (dehydration reaction by 3-hydroxyadipate dehydratase) to allow production of α-hydromuconic acid (hex-2-enedioate) (Patent Document 1, FIG. 3).

A case where 0.86 mg/L α-hydromuconic acid was produced in 17 days as *Desulfovirga adipica* grew while degrading adipic acid has also been reported (Non-patent Document 1).

PRIOR ART DOCUMENTS

Patent Document

[Patent Document 1] WO 2009/151728

Non-Patent Document

[Non-patent Document 1] Int J Syst Evol Microbiol. 2000 March; 50 Pt 2: 639-44.

SUMMARY OF THE INVENTION

Problems to be Solved by the Invention

Patent Document 1 describes that, in a microorganism which is artificially modified such that adipic acid can be produced, 3-hydroxyadipic acid (3-hydroxyadipate) as an intermediate of adipic acid, which is the product of interest, is dehydrated by an enzymatic reaction to allow production of α-hydromuconic acid (hex-2-enedioate). However, the document also describes that no direct evidence for the dehydration reaction from 3-hydroxyadipic acid to α-hydromuconic acid by 3-hydroxyadipate dehydratase has been found, and no test has been carried out for confirming whether α-hydromuconic acid can be actually produced using a metabolic pathway in a microorganism. Moreover, since the enzyme 3-hydroxyadipate dehydratase is not well known to those skilled in the art, production of α-hydromuconic acid using succinyl-CoA and acetyl-CoA as starting materials according to the description in Patent Document 1 has been impossible.

Although Non-patent Document 1 reports that α-hydromuconic acid is produced by a naturally occurring microorganism, the productivity is very low, and the method cannot therefore be said to be a method of producing α-hydromuconic acid.

Thus, there has practically been no method of producing α-hydromuconic acid using a metabolic pathway of a microorganism. In view of this, the present invention aims to provide a method of producing α-hydromuconic acid using a metabolic pathway in a microorganism.

Means for Solving the Problems

As a result of intensive study for solving the above problem, the present inventors discovered that a microorganism capable of producing α-hydromuconic acid using a metabolic pathway exists in nature, to reach the present invention.

That is, the present invention provides the following (1) to (13).

(1) A method of producing α-hydromuconic acid, the method comprising the step of culturing at least one type of microorganism having a capacity to produce α-hydromuconic acid, selected from the group consisting of microorganisms belonging to the genus *Escherichia*, microorganisms belonging to the genus *Pseudomonas*, microorganisms belonging to the genus *Hafnia*, microorganisms belonging to the genus *Bacillus*, microorganisms belonging to the genus *Cupriavidus*, microorganisms belonging to the genus *Acinetobacter*, microorganisms belonging to the genus *Alcaligenes*, microorganisms belonging to the genus *Delftia*, and microorganisms belonging to the genus *Shimwellia*.

(2) The method according to (1), wherein the microorganism is at least one selected from the group consisting of microorganisms belonging to the genus *Cupriavidus*, microorganisms belonging to the genus *Acinetobacter*, microorganisms belonging to the genus *Delftia*, microorganisms belonging to the genus *Shimwellia*, microorganisms belonging to the genus *Escherichia*, and microorganisms belonging to the genus *Pseudomonas*.

(3) The method according to (1) or (2), wherein the microorganism belonging to the genus *Escherichia* is *Escherichia fergusonii* or *Escherichia coli*.

(4) The method according to (1) or (2), wherein the microorganism belonging to the genus *Pseudomonas* is *Pseudomonas fluorescens*, *Pseudomonas putida*, *Pseudomonas azotoformans*, or *Pseudomonas chlororaphis* subsp. *aureofaciens*.

(5) The method according to (1), wherein the microorganism belonging to the genus *Hafnia* is *Hafnia alvei*.

(6) The method according to (1), wherein the microorganism belonging to the genus *Bacillus* is *Bacillus badius*.

(7) The method according to (1) or (2), wherein the microorganism belonging to the genus *Cupriavidus* is *Cupriavidus metallidurans*, *Cupriavidus numazuensis*, or *Cupriavidus oxalaticus*.

(8) The method according to (1) or (2), wherein the microorganism belonging to the genus *Acinetobacter* is *Acinetobacter baylyi* or *Acinetobacter radioresistens*.

(9) The method according to (1), wherein the microorganism belonging to the genus *Alcaligenes* is *Alcaligenes faecalis*.

(10) The method according to (1), wherein the microorganism belonging to the genus *Delftia* is *Delftia acidovorans*.

(11) The method according to (1) or (2), wherein the microorganism belonging to the genus *Shimwellia* is *Shimwellia blattae*.

(12) The method according to any one of (1) to (11), wherein a medium with which the microorganism is cultured contains at least one carbon source selected from the group consisting of saccharides, succinic acid, 2-oxoglutaric acid, and glycerol.

(13) The method according to any one of (1) to (12), wherein the microorganism is cultured with a medium containing at least one inducer selected from the group consisting of ferulic acid, p-coumaric acid, benzoic acid, cis,cis-muconic acid, protocatechuic acid, and catechol.

Effect of the Invention

By the present invention, α-hydromuconic acid can be produced using a metabolic pathway of a microorganism.

MODE FOR CARRYING OUT THE INVENTION

The method of producing α-hydromuconic acid of the present invention comprises the step of culturing a microorganism having a capacity to produce α-hydromuconic acid. More specifically, the present invention is characterized in that α-hydromuconic acid is produced using a metabolic pathway of a microorganism having a capacity to produce α-hydromuconic acid, by culturing the microorganism.

The microorganism having a capacity to produce α-hydromuconic acid used in the method of the present invention is selected from the following microorganisms.

Microorganisms belonging to the genus *Cupriavidus*
Microorganisms belonging to the genus *Acinetobacter*
Microorganisms belonging to the genus *Delftia*
Microorganisms belonging to the genus *Shimwellia*
Microorganisms belonging to the genus *Escherichia*
Microorganisms belonging to the genus *Pseudomonas*
Microorganisms belonging to the genus *Alcaligenes*
Microorganisms belonging to the genus *Bacillus*
Microorganisms belonging to the genus *Hafnia*

Specific examples of microorganisms having a capacity to produce α-hydromuconic acid and belonging to the genus *Cupriavidus* include *Cupriavidus metallidurans*, *Cupriavidus numazuensis*, and *Cupriavidus oxalaticus*. The mechanism by which microorganisms belonging to the genus *Cupriavidus* can produce α-hydromuconic acid using their metabolic pathway is not clear. Since the genus *Capriavidus* is known to degrade hydrocarbons derived from petroleum products such as benzene, toluene, and xylene (see JP 2007-252285 A), and to have metal tolerance (Antonie van Leeuwenhoek, 2009, 96, 2, 115-139), it is assumed that microorganisms belonging to the genus *Capriavidus* have a complex metabolic pathway which is different from those of microorganisms commonly used for matter production (for example, microorganisms belonging to the genus *Corynebacterium*), and that they produce α-hydromuconic acid based on this metabolic pathway.

Specific examples of microorganisms having a capacity to produce α-hydromuconic acid and belonging to the genus *Acinetobacter* include *Acinetobacter baylyi*. The mechanism by which microorganisms belonging to the genus *Acinetobacter* can produce α-hydromuconic acid using their metabolic pathway is also not clear. Since the genus *Acinetobacter* is known to degrade mineral oils such as benzene, fuel oils, and lubricating oils, and hence to be applicable to environmental cleanup (see JP 2013-123418 A), it is assumed that microorganisms belonging to the genus *Acinetobacter* have a complex metabolic pathway which is different from those of microorganisms commonly used for matter production (for example, microorganisms belonging to the genus *Corynebacterium*), and that they produce α-hydromuconic acid based on this metabolic pathway, similarly to the genus *Capriavidus*.

Specific examples of microorganisms having a capacity to produce α-hydromuconic acid and belonging to the genus *Delftia* include *Delftia acidovorans*. The mechanism by which microorganisms belonging to the genus *Delftia* can produce α-hydromuconic acid using their metabolic pathway is also not clear. Since the genus *Delftia* is known to degrade mineral oils such as benzene, fuel oils, and lubricating oils, and hence to be applicable to environmental cleanup (see JP 2013-123418 A), and to have metal tolerance (Journal of Water Resource and Protection, 2012, 4, 4, 207-216), it is assumed that microorganisms belonging to the genus *Delftia* have a complex metabolic pathway which is different from those of microorganisms commonly used for matter production (for example, microorganisms belonging to the genus *Corynebacterium*), and that they produce α-hydromuconic acid based on this metabolic pathway, similarly to the genus *Capriavidus* and the genus *Acinetobacter*.

Specific examples of microorganisms having a capacity to produce α-hydromuconic acid and belonging to the genus *Shimwellia* include *Shimwellia blattae*. The mechanism by which microorganisms belonging to the genus *Shimwellia* can produce α-hydromuconic acid using their metabolic pathway is also not clear. Since the genus *Shimwellia* is known to also inhabit a place where a radioactive radon concentration is high (see Radiation Protection and Environment, 2014, 37, 1, 21-24), it is assumed that microorganisms belonging to the genus *Shimwellia* have a complex metabolic pathway which is different from those of microorganisms commonly used for matter production (for example, microorganisms belonging to the genus *Corynebacterium*), and that they produce α-hydromuconic acid based on this metabolic pathway, similarly to the genus *Capriavidus*, the genus *Acinetobacter*, and the genus *Delftia*.

Specific examples of microorganisms having a capacity to produce α-hydromuconic acid and belonging to the genus *Escherichia* include *Escherichia fergusonii* and *Escherichia coli*. The mechanism by which microorganisms belonging to the genus *Escherichia* can produce α-hydromuconic acid using their metabolic pathway is also not clear. Since the genus *Escherichia* is known to have a hydrocarbon-degrading capacity and heavy metal tolerance (see Bioresource Technology, 2011, 102, 19, 9291-9295), it is assumed that microorganisms belonging to the genus *Escherichia* have a complex metabolic pathway which is different from those of microorganisms commonly used for matter production (for example, microorganisms belonging to the genus *Corynebacterium*), and that they produce α-hydromuconic acid based on this metabolic pathway, similarly to the genus *Capriavidus*, the genus *Acinetobacter*, the genus *Delftia*, and the genus *Shimwellia*.

Specific examples of microorganisms having a capacity to produce α-hydromuconic acid and belonging to the genus *Pseudomonas* include *Pseudomonas putida*. The mechanism by which microorganisms belonging to the genus *Pseudomonas* can produce α-hydromuconic acid using their metabolic pathway is also not clear. Since the genus *Pseudomonas* is known to degrade aromatic hydrocarbon-based solvents, petroleum hydrocarbon-based solvents, ester-based solvents, alcohol-based solvents, and the like (see JP 2010-130950 A), it is assumed that microorganisms belonging to the genus *Pseudomonas* have a complex metabolic pathway which is different from those of microorganisms commonly used for matter production (for example, microorganisms belonging to the genus *Corynebacterium*), and that they produce α-hydromuconic acid based on this metabolic pathway, similarly to the genus *Capriavidus*, the genus *Acinetobacter*, the genus *Delftia*, the genus *Shimwellia*, and the genus *Escherichia*.

Specific examples of microorganisms having a capacity to produce α-hydromuconic acid and belonging to the genus *Alcaligenes* include *Alcaligenes faecalis*. The mechanism by which microorganisms belonging to the genus *Alcaligenes* can produce α-hydromuconic acid using their metabolic pathway is also not clear. Since the genus *Alcaligenes* is used for purification of phenol compound-containing wastewater (see, JP 2016-41392 A), it is assumed that they have a complex metabolic pathway which is different from those of microorganisms commonly used for matter production, and that they produce α-hydromuconic acid based on this metabolic pathway.

Specific examples of microorganisms having a capacity to produce α-hydromuconic acid and belonging to the genus *Bacillus* include *Bacillus badius, Bacillus magaterium*, and *Bacillus roseus*. The mechanism by which microorganisms belonging to the genus *Bacillus* can produce α-hydromuconic acid using their metabolic pathway is also not clear. Since the genus *Bacillus* is used for wastewater processing systems in which wastewater is biologically treated with activated sludge (see JP 2006-305455 A), it is assumed that they have a complex metabolic pathway which is different from those of microorganisms commonly used for matter production, and that they produce α-hydromuconic acid based on this metabolic pathway.

Specific examples of microorganisms having a capacity to produce α-hydromuconic acid and belonging to the genus *Hafnia* include *Hafnia alvei*. The mechanism by which microorganisms belonging to the genus *Hafnia* can produce α-hydromuconic acid using their metabolic pathway is also not clear. Since the genus *Hafnia* is known to be tolerant to chromic acid contained in wastewater, and to degrade it (see J. bio-sci. 17: 71-76, 2009), it is assumed that they have a complex metabolic pathway which is different from those of microorganisms commonly used for matter production, and that they produce α-hydromuconic acid based on this metabolic pathway.

All of the microorganisms described above are known as microorganisms present in nature, and can be isolated from natural environments such as soils. They can also be purchased from microorganism-distributing agencies such as ATCC.

The microorganism may be one prepared by recombination of a gene(s) according to a known method, or one prepared by mutation by artificial mutation means, as long as the microorganism produces α-hydromuconic acid.

The fact that the microorganism has a capacity to produce α-hydromuconic acid can be confirmed by subjecting the supernatant of the culture liquid to an appropriate analysis method such as high-performance liquid chromatography (HPLC), high-performance liquid chromatography-mass spectrometry (LC/MS), high-performance liquid chromatography-tandem mass spectrometry (LC-MS/MS), gas chromatography (GC), or gas chromatography-mass spectrometry (GC/MS), to detect α-hydromuconic acid contained in the culture supernatant. In the present invention, it is preferred to use, as the microorganism having a capacity to produce α-hydromuconic acid, a microorganism capable of producing not less than 1.0 mg/L of α-hydromuconic acid in a culture supernatant obtained by culturing the microorganism for 20 hours to 48 hours.

In the method of the present invention, each of the microorganisms described above is cultured under conditions where α-hydromuconic acid is produced. In the present invention, the microorganism is cultured in a medium suitable for the microorganism used, for example, in a medium, preferably a liquid medium, containing a carbon source that can be metabolized by ordinary microorganisms. Here, the "metabolism" in the present invention means that a chemical substance which is incorporated from the outside of the cell or generated from another chemical substance in the cell by a microorganism is converted to another chemical substance by enzymatic reaction. In case where the microorganism is grown by culture, the medium preferably contains a carbon source assimilable by the microorganism cultured.

The medium used contains, besides the carbon source metabolizable by the microorganism used, suitable amounts of a metabolizable (preferably assimilable) nitrogen source, inorganic salt, and, if necessary, an organic micronutrient such as amino acid or vitamin. As long as the above nutrient sources are contained, the medium used may be either a natural medium or synthetic medium.

As the carbon source metabolizable by the microorganism, saccharides may be preferably used. Besides saccharides, any carbon source may be preferably used as long as it can be used as a sole carbon source for the growth of the microorganism. Specific examples of preferred carbon sources include monosaccharides such as glucose, sucrose, fructose, galactose, mannose, xylose, and arabinose; disaccharides and polysaccharides containing these monosaccharides bound to each other; starch saccharified liquids, molasses, and cellulose-containing biomass saccharified liquids containing these saccharides; organic acids such as acetic acid, succinic acid, lactic acid, fumaric acid, citric acid, propionic acid, malic acid, malonic acid, adipic acid, 2-oxoglutaric acid, and pyruvic acid; monovalent alcohols such as methanol, ethanol, and propanol; polyols such as glycerin, ethylene glycol, and propanediol; hydrocarbons; fatty acids; and oils. The carbon sources described above may be used either individually or in combination. More specifically, the microorganism can efficiently produce α-hydromuconic acid by metabolizing, among these carbon sources, one or more selected from the group consisting of saccharides, succinic acid, 2-oxoglutaric acid, and glycerol. The concentration of the saccharide(s) in the medium is not limited, and may be appropriately set depending on the type of the microorganism cultured, the type(s) of the saccharide(s), and/or the like. The concentration is usually about 5 g/L to 300 g/L.

Examples of the assimilable nitrogen source used for the culture of the microorganism include ammonia gas, aqueous ammonia, ammonium salts, urea, nitrates, and other supplementary organic nitrogen sources, for example, oil cakes, soybean hydrolysates, casein digests, other amino acids, vitamins, corn steep liquor, yeasts or yeast extracts, meat extracts, peptides such as peptone, and various fermentation microorganism cells and hydrolysates thereof. The concentration of the nitrogen source in the medium is not limited, and may be appropriately selected depending on the type of the microorganism cultured, the type of the nitrogen source, and/or the like. The concentration is usually about 0.1 g/L to 50 g/L.

Examples of inorganic salts which may be added as appropriate to be used for the culture of the microorganism include phosphoric acid salts, magnesium salts, calcium salts, iron salts, and manganese salts.

Conditions of the culture of the microorganism to be set for the production of α-hydromuconic acid, such as the medium having the component composition described above, culture temperature, stirring rate, pH, aeration rate, and inoculation amount, may be appropriately controlled or selected based on the type of the production microorganism used, external conditions, and/or the like. In cases where foaming occurs in the liquid culture, an antifoaming agent such a mineral oil, silicone oil, or surfactant may be included as appropriate in the medium. These culture conditions are known for each microorganism, and also specifically described in the following Examples.

By the medium and the culture conditions described above, α-hydromuconic acid can be produced by culture using the microorganism. More efficient production of α-hydromuconic acid is possible by culturing the microorganism in a state where a metabolic pathway required for the production of α-hydromuconic acid is activated. The method of activating the metabolic pathway is not limited, and examples of the method include a method in which the microorganism is cultured in a medium containing a substance that activates a metabolic pathway(s) (hereinafter also referred to as inducer) to induce expression of an enzyme gene(s) in a metabolic pathway(s) for the production of α-hydromuconic acid, a method in which a coding region(s) of an enzyme gene(s) and/or a functional region(s) in the vicinity thereof is/are modified by a gene modification technique, a method in which the copy number(s) of an enzyme gene(s) is/are increased, and a method in which an enzyme gene function(s) in a biosynthetic pathway(s) of a by-product(s) is/are destroyed. The method is preferably a method in which expression of an enzyme gene(s) in a metabolic pathway(s) for the production of α-hydromuconic acid is induced by an inducer(s).

The inducer is not limited as long as it is a substance that activates a metabolic pathway required for the production of α-hydromuconic acid. Examples of the inducers which may be usually used include aromatic compounds, and aliphatic compounds having a carbon number of not less than 6, preferably 6 to 30, which are metabolized into compounds having smaller carbon numbers through 3-oxoadipyl-CoA as an intermediate. The aliphatic compound having a carbon number of not less than 6 is preferably a dicarboxylic acid having a carbon number of not less than 6, preferably 6 to 30. Examples of such a compound can be known using a database such as KEGG (Kyoto Encyclopedia of Genes and Genomes). Specific examples of the compound include adipic acid, benzoic acid, cis,cis-muconic acid, terephthalic acid, protocatechuic acid, catechol, vanillin, coumaric acid, and ferulic acid. Preferred examples of the compound include adipic acid, ferulic acid, and p-coumaric acid.

The above inducers may be used either individually or in combination of two or more thereof depending on the microorganism used for the production of α-hydromuconic acid. The inducer may be contained in the medium used in culture for growing the microorganism (preculture) in a stage preceding the production of α-hydromuconic acid, or may be contained in the medium used for the production of α-hydromuconic acid. In cases where one or more inducers are contained in the medium, the concentration of the inducer(s) (total concentration in cases where a plurality of inducers are contained) is not limited, and appropriately selected depending on the type of the microorganism, type(s) of the inducer(s), and the like. The concentration is usually 1 mg/L to 10 g/L, preferably 5 mg/L to 1 g/L.

After allowing production of α-hydromuconic acid in the culture of the microorganism to an amount at which α-hydromuconic acid can be recovered, the α-hydromuconic acid produced can be recovered. The recovery, for example, isolation, of the α-hydromuconic acid produced can be carried out according to a general method in which the culture is stopped at a time point when accumulation of the product proceeded to an appropriate level, and then a fermentation product is collected from the culture. More specifically, for example, after separating microbial cells by centrifugation, filtration, and/or the like, α-hydromuconic acid can be isolated from the culture by column chromatography, ion-exchange chromatography, activated carbon treatment, crystallization, membrane separation, and/or the like. Still more specifically, preferred examples of the recovering method include, but are not limited to, a method in which the culture is subjected to removal of water by a concentration operation using a reverse osmosis membrane, evaporator, and/or the like to increase the concentration of α-hydromuconic acid, and crystals of α-hydromuconic acid and/or a salt of α-hydromuconic acid are precipitated by cooling crystallization or insulated crystallization, followed by obtaining crystals of α-hydromuconic acid and/or the salt of α-hydromuconic acid by centrifugation, filtration, and/or the like, and a method in which alcohol is added to the culture to produce α-hydromuconic acid ester, and then the α-hydromuconic acid ester is recovered by a distillation operation, followed by performing hydrolysis to obtain α-hydromuconic acid.

EXAMPLES

The present invention is described below concretely by way of Examples. However, the present invention is not limited to these.

Reference Example 1 Preparation of α-Hydromuconic Acid

The α-hydromuconic acid used in the analysis in the Examples described below was prepared by chemical synthesis. First, 1.5 L of super-dehydrated tetrahydrofuran (manufactured by Wako Pure Chemical Industries, Ltd.) was added to 13.2 g (0.1 mol) of succinic acid monomethyl ester (manufactured by Wako Pure Chemical Industries, Ltd.), and 16.2 g (0.1 mol) of carbonyldiimidazole (manufactured by Wako Pure Chemical Industries, Ltd.) was added thereto with stirring, followed by stirring the resulting mixture under nitrogen atmosphere for 1 hour at room temperature. To this suspension, 15.6 g (0.1 mol) of malonic acid monomethyl ester potassium salt and 9.5 g (0.1 mol) of magnesium chloride were added. The resulting mixture was stirred under nitrogen atmosphere for 1 hour at room temperature, and then stirred at 40° C. for 12 hours. After the reaction, 0.05 L of 1 mol/L hydrochloric acid was added to the mixture, and extraction with ethyl acetate was carried out. By separation purification by silica gel column chromatography (hexane:ethyl acetate=1:5), 13.1 g of pure 3-oxohexanedicarboxylic acid dimethyl ester was obtained. Yield: 70%.

To 10 g (0.05 mol) of the 3-oxohexanedicarboxylic acid dimethyl ester obtained, 0.1 L of methanol (manufactured by Kokusan Chemical Co., Ltd.) was added, and 2.0 g (0.05 mol) of sodium borohydride (manufactured by Wako Pure Chemical Industries, Ltd.) was added to the resulting mixture with stirring, followed by stirring the mixture at room temperature for 1 hour. Subsequently, 0.02 L of 5 mol/L aqueous sodium hydroxide solution was added to the mixture, and the mixture was then stirred at room temperature for 2 hours. After the reaction, the pH was adjusted to 1 with 5 mol/L hydrochloric acid. The reaction liquid was then concentrated using a rotary evaporator. By recrystallization with water, 7.2 g of pure α-hydromuconic acid was obtained. Yield: 95%.

$^1$H-NMR Spectrum of α-Hydromuconic Acid:
$^1$H-NMR (400 MHz, CD$_3$OD): δ2.48 (m, 4H), 65.84 (d, 1H), 66.96 (m, 1H).

Example 1 α-Hydromuconic Acid Production Test Using Succinic Acid Microbial Culture The α-hydromuconic acid productivities of the microorganisms shown in Table 1 (all microorganisms were purchased from microorganism-distributing agencies; the distributors are described in the strain names) were investigated. To 5 mL of a medium containing 10 g/L tryptone, 5 g/L yeast extract, 5 g/L sodium chloride, and 0.5 g/L adipic acid (pH 7), a loopful of each microorganism was inoculated, and shake culture was carried out at 30° C. until the microorganism was sufficiently suspended (preculture). To the culture liquid, 10 mL of 0.9% sodium chloride was added, and the microbial cells were centrifuged, followed by completely removing the supernatant, thereby washing the microbial cells. After carrying out this operation three times, the microbial cells were suspended in 1 mL of 0.9% sodium chloride. To 5 mL of the medium having the following composition containing succinic acid as a carbon source, 0.5 mL of the resulting suspension was added, and shake culture was performed at 30° C. for 20 hours (main culture). The main culture liquid was subjected to centrifugation to separate microbial cells, and the resulting supernatant was analyzed by LC-MS/MS.

Medium Composition for the Main Culture:
20 g/L succinic acid
2 g/L ammonium sulfate
100 mM potassium phosphate
0.05 g/L magnesium sulfate
0.125 mg/L iron sulfate
5.4 mg/L manganese sulfate
0.66 mg/L calcium chloride
0.25 g/L yeast extract
pH 6.5.
Quantitative Analysis of α-Hydromuconic Acid
Quantitative analysis of α-hydromuconic acid by LC-MS/MS was carried out under the following conditions.
HPLC: 1290 Infinity (manufactured by Agilent Technologies)
Column: Synergi hydro-RP (manufactured by Phenomenex); length, 100 mm; inner diameter, 3 mm; particle size, 2.5 μm
Mobile phase: 0.1% aqueous formic acid solution/methanol=70/30
Flow rate: 0.3 mL/minute
Column temperature: 40° C.
LC detector: DAD (210 nm)
MS/MS: Triple-Quad LC/MS (manufactured by Agilent Technologies) Ionization method: ESI negative mode.

The concentration of α-hydromuconic acid accumulated in the culture supernatant was as shown in Table 1. It was confirmed that all microorganisms have a capacity to produce α-hydromuconic acid.

TABLE 1

| Test microorganism | α-Hydromuconic acid (mg/L) |
|---|---|
| Cupriavidus metallidurans NBRC101272 | 11 |
| Cupriavidus numazuensis NBRC100056 | 1.1 |

TABLE 1-continued

| Test microorganism | α-Hydromuconic acid (mg/L) |
|---|---|
| Cupriavidus oxalaticus NBRC13593 | 1.0 |
| Cupriavidus sp. NBRC102508 | 2.4 |
| Acinetobacter baylyi ATCC33305 | 1.3 |
| Acinetobacter sp. NBRC100985 | 2.9 |
| Delftia acidovorans ATCC11299 | 1.0 |
| Shimwellia blattae NBRC105725 | 1.2 |
| Escherichia fergusonii NBRC102419 | 1.4 |
| Escherichia coli NBRC12713 | 1.5 |
| Pseudomonas sp. NBRC12691 | 1.0 |
| Pseudomonas putida NBRC12996 | 2.3 |
| Pseudomonas sp. ATCC15915 | 1.8 |

Example 2 Production Example of α-Hydromuconic Acid

To 5 mL of LB medium, a loopful of Cupriavidus metallidurans NBRC101272, which was confirmed to be a microorganism having a capacity to produce α-hydromuconic acid in Example 1, was inoculated, and shake culture was carried out at 30° C. until the microorganism was sufficiently suspended (pre-preculture). To 100 mL of a medium containing 10 g/L tryptone, 5 g/L yeast extract, 5 g/L sodium chloride, and 0.5 g/L adipic acid (pH 7), 2 mL of the pre-preculture liquid was added, and shake culture was carried out at 30° C. until the microorganism was sufficiently suspended (preculture). After removing the pre-culture liquid by washing with 200 mL of 0.9% sodium chloride three times in the same manner as in Example 1, the microbial cells were suspended in 10 mL of 0.9% sodium chloride.

To 100 mL of the same main culture medium containing succinic acid as a carbon source as in Example 1, 10 mL of the resulting suspension was added, and shake culture was performed at 30° C. for 20 hours (main culture). The main culture liquid was subjected to centrifugation to separate microbial cells, and the resulting supernatant was analyzed by LC-MS/MS in the same manner as in Example 1. As a result, the concentration of α-hydromuconic acid accumulated in the culture supernatant was found to be 13 mg/L.

Subsequently, the supernatant from the main culture was concentrated under reduced pressure, to obtain 11 mL of a concentrate having an α-hydromuconic acid concentration of 120 mg/L. The resulting concentrate was injected into HPLC to which a fraction collection device was connected, and a fraction having the same elution time as an α-hydromuconic acid sample was collected. This operation was carried out ten times for removal of impurities in the culture liquid, to obtain an aqueous α-hydromuconic acid solution. The preparative HPLC used for the collection of α-hydromuconic acid was carried out under the following conditions.
HPLC: SHIMADZU 20A (manufactured by Shimadzu Corporation)
Column: Synergi hydro-RP (manufactured by Phenomenex); length, 250 mm; inner diameter, 10 mm; particle size, 4 μm
Mobile phase: 5 mM aqueous formic acid solution/acetonitrile=98/2
Flow rate: 4 mL/minute
Injection volume: 1 mL
Column temperature: 45° C.
Detector: UV-VIS (210 nm)
Fraction collection device: FC204 (manufactured by Gilson)
Subsequently, the aqueous α-hydromuconic acid solution was concentrated under reduced pressure, to obtain 1.1 mg of crystals. As a result of analysis of the crystals by ¹H-NMR, the obtained crystals was confirmed to be α-hydromuconic acid.

Comparative Example 1 Microorganisms Having No Capacity to Produce α-Hydromuconic Acid In order to investigate the α-hydromuconic acid productivities of the microorganisms shown in Table 2, culture was carried out under the same conditions as in Example 1, and quantitative analysis of α-hydromuconic acid was carried out. As a result, no α-hydromuconic acid was detected in the culture supernatants.

TABLE 2

| Test microorganism | α-Hydromuconic acid (mg/L) |
| --- | --- |
| Corynebacterium glutamicum ATCC13032 | N.D. |
| Zymomonas mobilis NBRC13756 | N.D. |

Comparative Example 2 Culture without Addition of Carbon Source

The microorganisms shown in Table 1 were cultured under the same conditions as in Example 1 except that a medium having a composition containing no succinic acid was used. As a result of quantitative analysis of α-hydromuconic acid, no α-hydromuconic acid was detected in the culture supernatant. By this, it was confirmed that the α-hydromuconic acid quantified in Example 1 was produced as a result of metabolism of succinic acid.

Example 3 α-Hydromuconic Acid Production Test Using Various Microorganisms

The microorganisms shown in Table 3 (all microorganisms were purchased from microorganism-distributing agencies; the distributors are described in the strain names) were subjected to preculture and microbial cell washing under the same conditions as in Example 1 except that each of ferulic acid, p-coumaric acid, benzoic acid, cis,cis-muconic acid, protocatechuic acid, and catechol was added to 2.5 mM as an inducer to the preculture medium. To 5 mL of the medium having the composition shown below, 0.5 mL of the washed suspension was added, and shake culture was performed at 30° C. for 48 hours.
10 g/L succinic acid
10 g/L glucose
10 g/L glycerol
1 g/L ammonium sulfate
50 mM potassium phosphate
0.025 g/L magnesium sulfate
0.0625 mg/L iron sulfate
2.7 mg/L manganese sulfate
0.33 mg/L calcium chloride
1.25 g/L sodium chloride
2.5 g/L Bacto tryptone
1.25 g/L yeast extract
pH 6.5.

The results of quantitative analysis of α-hydromuconic acid accumulated in the culture supernatant are shown in Table 3. From these results, it was confirmed that all microorganisms have a capacity to produce α-hydromuconic acid.

TABLE 3

| Test microorganism | α-Hydromuconic acid production (mg/L) |
| --- | --- |
| Acinetobacter radioresistens NBRC102413 | 1.1 |
| Alcaligenes faecalis NBRC13111 | 2.8 |
| Bacillus badius ATCC14574 | 1.1 |
| Escherichia coli NBRC12713 | 3.3 |
| Hafnia alvei ATCC9760 | 12.0 |
| Hafnia alvei NBRC3731 | 14.8 |
| Pseudomonas fluorescens NBRC3081 | 2.4 |
| Pseudomonas putida NBRC12653 | 17.4 |
| Pseudomonas putida NBRC3738 | 5.6 |
| Pseudomonas putida ATCC17642 | 6.1 |
| Pseudomonas putida NBRC12996 | 2.2 |
| Pseudomonas putida ATCC15070 | 1.5 |
| Pseudomonas putida ATCC15175 | 4.0 |
| Pseudomonas putida ATCC8209 | 5.7 |
| Pseudomonas sp. ATCC17472 | 1.0 |
| Pseudomonas azotoformans NBRC12693 | 1.0 |
| Pseudomonas chlororaphis subsp. aureofaciens NBRC3521 | 7.2 |
| Pseudomonas putida NBRC100650 | 2.5 |

Example 4 α-Hydromuconic Acid Production Test without Addition of Inducers

The microorganisms shown in Table 4 were subjected to preculture and microbial cell washing under the same conditions as in Example 3 except that the inducer used in Example 3 was not added. To 5 mL of the medium having the composition shown below, 0.5 mL of the washed suspension was added, and shake culture was performed at 30° C. for 48 hours.
10 g/L succinic acid
10 g/L glucose
1 g/L ammonium sulfate
50 mM potassium phosphate
0.025 g/L magnesium sulfate
0.0625 mg/L iron sulfate
2.7 mg/L manganese sulfate
0.33 mg/L calcium chloride
1.25 g/L sodium chloride
2.5 g/L Bacto tryptone
1.25 g/L yeast extract
pH 6.5.

The results of quantitative analysis of α-hydromuconic acid in the culture supernatant are shown in Table 4.

From these results, it was confirmed that the microorganisms shown in Table 4 have a capacity to produce α-hydromuconic acid even in cases where preculture is carried out without addition of an inducer.

TABLE 4

| Test microorganism | α-Hydromuconic acid production (mg/L) |
| --- | --- |
| Alcaligenes faecalis NBRC13111 | 1.3 |
| Escherichia coli NBRC12713 | 1.2 |
| Hafnia alvei NBRC3731 | 1.4 |
| Hafnia alvei ATCC9760 | 2.4 |
| Pseudomonas putida NBRC12653 | 1.0 |
| Pseudomonas putida NBRC3738 | 1.1 |
| Pseudomonas putida ATCC15175 | 1.0 |
| Pseudomonas putida ATCC8209 | 1.2 |
| Pseudomonas azotoformans NBRC12996 | 1.3 |
| Pseudomonas chlororaphis subsp. aureofaciens NBRC3521 | 1.2 |

Example 5 α-Hydromuconic Acid Production Test
Using p-Coumaric Acid or Ferulic Acid as Inducer The microorganisms shown in Table 5 were subjected to preculture and microbial cell washing under the same conditions as in Example 4 except that p-coumaric acid or ferulic acid, among the substances added as inducers to the preculture medium in Example 3, was added to 0.5 mM. To 5 mL of the medium having the composition shown below, 0.5 mL of the washed suspension was added, and shake culture was performed at 30° C. for 48 hours. The results of quantitative analysis of α-hydromuconic acid in the culture supernatant are shown in Table 5. From these results, it was found that the productivity of α-hydromuconic acid can be increased even by addition of p-coumaric acid or ferulic acid alone as an inducer to the preculture medium compared to cases where neither of these is added.

TABLE 5

| Test microorganism | α-Hydromuconic acid production (mg/L) | | |
| --- | --- | --- | --- |
| | No addition | p-coumaric acid added | Ferulic acid added |
| *Alcaligenes faecalis* NBRC13111 | 1.3 | 1.6 | 1.7 |
| *Escherichia coli* NBRC12713 | 1.2 | 1.9 | 2.0 |
| *Hafnia alvei* NBRC3731 | 1.4 | 5.6 | 2.0 |
| *Hafnia alvei* ATCC9760 | 2.4 | 3.3 | 3.7 |
| *Pseudomonas putida* NBRC12653 | 1.0 | 2.1 | 2.3 |
| *Pseudomonas putida* NBRC3738 | 1.1 | 1.5 | 2.3 |
| *Pseudomonas putida* ATCC15175 | 1.0 | 3.0 | 3.4 |
| *Pseudomonas putida* ATCC8209 | 1.2 | 1.9 | 2.5 |
| *Pseudomonas azotoformans* NBRC12996 | 1.3 | 1.6 | 1.7 |
| *Pseudomonas chlororaphis* subsp. *aureofaciens* NBRC3521 | 1.2 | 1.6 | 1.7 |

INDUSTRIAL APPLICABILITY

By the present invention, α-hydromuconic acid can be produced using a microorganism. The obtained α-hydromuconic acid can be used as a raw material for polymers.

The invention claimed is:

1. A method of producing α-hydromuconic acid, said method comprising the step of culturing at least one type of microorganism having a capacity to produce α-hydromuconic acid, selected from the group consisting of microorganisms belonging to genus *Escherichia*, microorganisms belonging to genus *Pseudomonas*, microorganisms belonging to genus *Hafnia*, microorganisms belonging to genus *Bacillus*, microorganisms belonging to genus *Cupriavidus*, microorganisms belonging to genus *Acinetobacter*, microorganisms belonging to genus *Alcaligenes*, microorganisms belonging to genus *Delftia*, and microorganisms belonging to genus *Shimwellia*; and recovering the produced α-hydromuconic acid;
said microorganism(s) metabolize(s) succinic acid into α-hydromuconic acid.

2. The method of claim 1, wherein said microorganism is at least one selected from the group consisting of microorganisms belonging to genus *Cupriavidus*, microorganisms belonging to genus *Acinetobacter*, microorganisms belonging to genus *Delftia*, microorganisms belonging to genus *Shimwellia*, microorganisms belonging to genus *Escherichia*, and microorganisms belonging to genus *Pseudomonas*.

3. The method of claim 1, wherein said microorganism belonging to genus *Escherichia* is *Escherichia fergusonii* or *Escherichia coli*.

4. The method of claim 1, wherein said microorganism belonging to genus *Pseudomonas* is *Pseudomonas fluorescens*, *Pseudomonas putida*, *Pseudomonas azotoformans*, or *Pseudomonas chlororaphis* subsp. *aureofaciens*.

5. The method of claim 1, wherein said microorganism belonging to genus *Hafnia* is *Hafnia alvei*.

6. The method of claim 1, wherein said microorganism belonging to genus *Bacillus* is *Bacillus badius*.

7. The method of claim 1, wherein said microorganism belonging to genus *Cupriavidus* is *Cupriavidus metallidurans*, *Cupriavidus numazuensis*, or *Cupriavidus oxalaticus*.

8. The method of claim 1, wherein said microorganism belonging to genus *Acinetobacter* is *Acinetobacter baylyi* or *Acinetobacter radioresistens*.

9. The method of claim 1, wherein said microorganism belonging to genus *Alcaligenes* is *Alcaligenes faecalis*.

10. The method of claim 1, wherein said microorganism belonging to genus *Delftia* is *Delftia acidovorans*.

11. The method of claim 1, wherein said microorganism belonging to genus *Shimwellia* is *Shimwellia blattae*.

12. The method of claim 1, wherein said microorganism is cultured with a medium containing at least one inducer selected from the group consisting of ferulic acid, p-coumaric acid, benzoic acid, cis,cis-muconic acid, protocatechuic acid, and catechol.

* * * * *